United States Patent [19]

Austin

[11] Patent Number: 6,005,032
[45] Date of Patent: Dec. 21, 1999

[54] COMPOSITION AND USE

[75] Inventor: Peter William Austin, Bury, United Kingdom

[73] Assignee: Zeneca Limited, London, United Kingdom

[21] Appl. No.: 08/860,280

[22] PCT Filed: Dec. 18, 1995

[86] PCT No.: PCT/GB95/02951

§ 371 Date: Jun. 17, 1997

§ 102(e) Date: Jun. 17, 1997

[87] PCT Pub. No.: WO96/22023

PCT Pub. Date: Jul. 25, 1996

[30] Foreign Application Priority Data

Jan. 17, 1995 [GB] United Kingdom .................... 9500856

[51] Int. Cl.$^6$ ........................................................ C08K 5/45

[52] U.S. Cl. .................................. 524/82; 524/83; 524/84
[58] Field of Search ................................... 524/82, 83, 84

[56] References Cited

U.S. PATENT DOCUMENTS 5,246,812  9/1993  von Trebra et al. ..................... 430/253

FOREIGN PATENT DOCUMENTS 1531431  11/1978  United Kingdom .
94/20479  9/1994  WIPO .

*Primary Examiner*—Edward J. Cain
*Attorney, Agent, or Firm*—Pillsbury, Madison & Sutro LLP

[57] ABSTRACT

The use of a 2-($C_{3-5}$-alkyl)-BIT or 2-aralkyl-BIT such as 2-phenylethyl-BIT as a fungicide for plastics materials. 2-n-Butyl-BIT is preferred.

16 Claims, No Drawings

COMPOSITION AND USE

This application is the national phase of international application PCT/GB95/02951, filed Dec. 18, 1995 which was designated the U.S.

The present invention relates to the use of 2-alkyl- and 2-aralkyl-1,2-benzisothiazolin-3-ones as biocides for the protection of plastics materials and especially their use as fungicides, including compositions thereof. 1,2-benzisothiazolin-3-ones (hereinafter "BIT") and their use as biocides are well known to the art.

GB 848,130 discloses BIT's containing inter alia a 2-alkyl substituent containing at least 4 carbon atoms or a 2-benzyl group substituted by halogen. These compounds are said to possess useful anti-bacterial and antifungal activity and are of use as pharmaceutical, vetinary and agricultural biocides.

U.S. Pat. No. 3,517,022 discloses BIT's containing inter alia a 2-alkyl substituent having from 4 to 24 carbon atoms and where the phenyl ring of the BIT is substituted by halogen, $C_{1-4}$-alkyl or $C_{1-4}$-alkoxy. Such compounds are said to be useful industrial biocides, especially agricultural fungicides and also pesticides.

GB 1,531,431 discloses 2-($C_{1-3}$-alkyl)-BIT's and their use as industrial biocides, including fungicides, in aqueous systems and paint films.

More recently, EP 475,123 has proposed the use of 2-(n-$C_{6-8}$-alkyl)-BIT's as industrial biocides and especially fungicides for paint and plastics materials. These compounds are said to be particularly effective against *Scopulariopsis brevicaulis*. Furthermore, the 2-(n-$C_{6-8}$-alkyl)-BIT's are stated to have much higher activity against mould fungi that the 2-($C_{1-3}$-alkyl)-BIT's of GB 1,531,431. Indeed, data is presented which shows that the 2-n-octyl-BIT is more active than 2-n-hexyl-BIT and both are significantly more active than 2-methyl-BIT against fungi and yeast.

It has now been found that some 2-alkyl-BIT derivatives are very active against fungal deteriogens for plastics materials and contrary to the recent teachings of EP 475,123 the activity of these compounds against the important fungi in plastics materials actually decreases with increasing number of carbon atoms in the 2-alkyl chain. It has also been found that some 2-aralkyl-BIT derivatives are also very active against these particular fungi in plastics materials.

A further important property which is required by a fungicide for plastics materials is the ability to withstand the processing conditions to which the material is subjected during fabrication processes such as extrusion. This generally involves heating the plastics materials at temperatures in excess of 140° C. It is therefore important that the fungicide exhibits high temperature stability and low volatility under such conditions.

It has now been found that the more active BIT-derivatives exhibit too high a volatility to make than suitable as fungicides for plastics materials and that the 2-alkyl group must contain not less than 3 carbon atoms. The 2-aralkyl-BIT derivatives exhibit acceptable and very advantageous low volatility.

A still further important requirement for a fungicide for plastics materials is that it must be capable of formulation with plasticisers and stabilisers which are commonly used in the plastics materials fabrication industry and that the fungicide exhibits high resistance to discoloration in use and longevity of effect under various conditions to which the treated plastics materials are exposed in use.

It has been found that certain 2-alkyl and 2-aralkyl BIT derivatives (hereinafter "ABIT") meet the aforementioned requirements especially in respect of volatility and activity against fungal deteriogens for plastics materials.

According to the invention there is provided the use of 2-alkyl- and 2-aralkyl-BIT derivatives of Formula 1 as fungicides for plastics materials

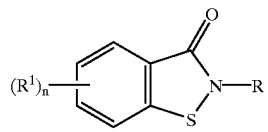

wherein
$R^1$ is hydroxy, halogen, $C_{1-4}$-alkyl or $C_{1-4}$-alkoxy;
R is $C_{3-5}$-alkyl, cycloalkyl or aralkyl which contains at least 2 carbon atoms linking the aryl group to the nitrogen atom and where the alkyl or aryl group may be optionally substituted; and
n is from 0 to 4.

Preferably, halogen is bromine and especially chlorine.

The substituent $R^1$ is preferably located in the 5- and/or 6-position of the BIT molecule and is especially located in the 6-position.

An especially preferred embodiment is where n is zero.

When R is alkyl it may be linear or branched but is preferably linear. Examples of such alkyl groups are n-propyl, iso-propyl, n-butyl, iso-butyl, tert-butyl, n-amyl, iso-amyl and 2-methylbutyl.

When R is cycloalkyl it is preferably cyclopentyl.

When R is alkyl, it preferably contains 4 carbon atoms and is especially n-butyl.

When R is aralkyl, it is preferably 2-arylethyl and especially 2-phenylethyl.

When the alkyl group or the aryl moiety of the aralkyl group represented by R is substituted, the substituent is preferably hydroxy, halogen or nitrile. It is preferred, however, that the alkyl group and the aryl moiety are unsubstituted.

Particularly useful effects have been obtained when R is n-butyl and especially 2-phenylethyl.

The ABIT is incorporated in the plastics materials to be protected at a concentration from that at which the ABIT exhibits some control of fungal growth up to much higher concentrations. Preferably, the amount of ABIT is less than 1.5%, more preferably less than 1.0%, particularly less than 0.7% and especially less than 0.5% by weight based on the weight of plastics material. Useful effects have been obtained when the amount of ABIT is less than 0.25% and even less than 0.1% by weight of the plastics materials.

The ABIT must be stable to the temperature conditions at which the plastics material is fabricated. Preferably, it is stable above 180° C., more preferably above 200° C. and especially above 250° C. It is preferred that the weight loss on heating from 25 to 160° C. at a heating rate of 10° C./minute is less than 10%, more preferably less than 6% and especially less than 2%.

As noted hereinbefore the ABIT is commonly formulated with a plasticiser or stabiliser which is suitable for use with the plastics material to be protected. Thus, according to a further aspect of the invention there is provided a composition comprising a plasticiser or stabiliser and an ABIT.

The plasticiser or stabiliser is any of those commonly used in the plastics fabrication industry. It is preferably a liquid and is especially an ester derived from mono- and di-carboxylic acids and linear or branched alcohols, epoxidised fatty acid ester and epoxidised vegetable oils. Examples of these plasticisers and stabilisers are phthalates, particularly dialkyl phthalates, such as dioctyl phthalate, di-(2-ethylhexyl) phthalate, dinonylphthalate and di-isodecylphthalate, epoxidised octyl stearate and epoxidised soya bean oil; and the phosphate esters of general formula O=P (OR$^2$)$_3$ wherein R$^2$ is hydrocarbyl, especially aryl such as phenyl and more especially C$_{1-4}$-alkyl which may be linear or branched. Examples of such alkyl groups are methyl, ethyl, isopropyl, butyl and tert-butyl. Examples of other esters are adipates, sebacates and trimellitates of linear or branched alcohols, especially those alcohols containing form 8 to 10 carbon atoms and low molecular weight oligo- and poly-esters such as those obtainable by reacting 1,3-butanediol with adipic acid.

The composition may contain more than one ABIT. It may also contain other fungicides and/or algicides in order to broaden the spectrum of activity of the composition. Examples of other fungicides and algicides include 2-alkyl-BIT's such as 2-(n-hexyl)-BIT, 2-(2-ethylbutyl)-BIT, 2-(2-ethylhexyl)-BIT, 2-octylisothiazolin-3-one, oxy-bis-10,10-phenoxarsine, trichloromethylmercaptophthalimide; ureas such as 2-(3,4-dichlorophenyl)-1,1-dimethylurea and 2-(4-isopropylphenyl)-1,1-dimethylurea; 4-alkylsulphonyl halogenated pyridines such as 2,3,5,6-tetrachloro-4 (methylsulphonyl)-pyridine and 2,3,6-trichloro-4 (isopropylsulphonyl)-pyridine; tetrachloro-isophthalonitrile; benzimidazomethyl-carbamate; thiocyanatomethylthiobenzthiazole; methylene bisthiocyanate, iodopropargyl-n-butyl-carbamate; triazines such as 2-tert-butylamino-4-ethylamino-6-methylmercapto-1,3,5-triazine and 2-methylthio-4-tert-butylamino-6-cyclopropylamino-1,3,5-triazine; N-(1-methyl-1-naphthyl) maleamide; dichlorofluanide, (fluoro)-captan and (fluoro)-folpet.

Where the composition contains an additional fungicide and/or algicide it is present preferably at a concentration of less than 50%, more preferably less than 30% and especially less than 10% by weight relative to the amount of ABIT.

As mentioned hereinbefore, fungicides for plastics materials require a careful balance of microbiological activity and volatility and hence any additional fungicide and/or algicide should not significantly impair the properties and performance in use of the ABIT. For this reason it is preferred that the composition contains only an ABIT.

The 2-alkyl-BIT's of formula 1 are generally liquids at 20 to 25° C. and readily dissolve in the plasticiser or stabiliser. The aralkyl-BIT's are solids at 20 to 25° C. but can be readily dissolved in the plasticiser or stabiliser if necessary by heating.

Where higher concentrations of the ABIT are required in the plasticiser or stabiliser and this exceeds its solubility the ABIT may be dispersed in the plasticiser or stabiliser by means of a suitable dispersant particularly a non-ionic dispersant. One preferred dispersant is the reaction product of a hydroxy carboxylic acid and an amine, or a salt thereof.

Especially preferred are the dispersing agents of formula 2

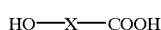

wherein

Z is a divalent bridging group which is attached to the carbonyl group through an oxygen or nitrogen atom;

R$^3$ is a primary, secondary or tertiary amino group or a salt thereof with an acid, or a quaternary ammonium salt; and Y is a the residue of a polyester chain which together with the —CO— group is derived from a hydroxycarboxylic acid of formula 3

HO—X—COOH  3 wherein X is a divalent saturated or unsaturated aliphatic group containing at least 8 carbon atoms and in which there are at least 4 carbon atoms between the hydroxy and carboxylic acid groups, or from a mixture of such a hydroxycarboxylic acid and a carboxylic acid which is free from hydroxy groups.

The group X is preferably an alkylene or alkenylene group and preferably contains not greater than 30 carbon atoms, and especially not greater than 20 carbon atoms. Examples of suitable hydroxy carboxylic acids of formula 3 are 12-hydroxystearic acid, ricinoleic acid, 12-hydroxydecanoic acid and 6-hydroxycaproic acid.

The divalent bridging group represented by Z is preferably of the formula

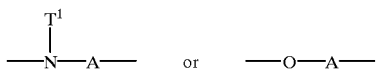

wherein T$^1$ is a hydrogen atom, a C$_{1-22}$-alkyl group or ethylene and A is an alkylene, cycloalkylene, heterocycloalkylene or a hydroxyalkylene group containing from 2 to 6 carbon atoms. When T$^1$ is alkyl, it is preferably C$_{1-6}$-alkyl and when A is heterocycloalkylene it is preferably piperazine. Where T$^1$ and A are both ethylene, the groups T$^1$ and A together with the nitrogen atom to which they are attached and the nitrogen atom of the amino group R$^3$ may form a piperazine ring.

As examples of the radicals represented by T$^1$ there may be mentioned methyl, ethyl, n-propyl, n-butyl and octadecyl. As examples of the radicals represented by A there may be mentioned ethylene, trimethylene, tetramethylene, hexamethylene and beta-hydroxytrimethylene.

The primary, secondary and tertiary amino groups represented by R$^3$ are preferably of the formula

wherein T$^2$ and T$^3$ are each independently hydrogen, C$_{1-22}$-alkyl, substituted C$_{1-22}$-alkyl, aralkyl, cycloalkyl, or T$^2$ and T$^3$ may together with the nitrogen atom to which they are attached form a 5- or 6-membered ring. When T$^2$ or T$^3$ is alkyl, it is preferably C$_{1-6}$-alkyl, such as methyl. When T$^2$ or T$^3$ is cycloalkyl, it is preferably cyclohexyl and when T$^2$ and T$^3$ form a ring it is preferably a piperidino, morpholino, or especially a piperazino ring. When T$^2$ or T$^3$ is aralkyl it is preferably benzyl.

The quaternary ammonium groups represented by R$^3$ are preferably of the formula

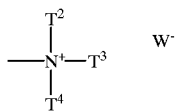

wherein $T^4$ is hydrogen, $C_{1-22}$-alkyl, substituted $C_{1-22}$-alkyl, aralkyl or cycloalkyl and $\overline{W}$ is an anion. It is preferred that $T^4$ is $C_{1-6}$-alkyl, such as methyl.

In the special case where $T^2$ and $T^3$ together with the nitrogen atom to which they are attached forms a piperazino ring, either or both nitrogen atoms may be alkylated and either ring nitrogen may form a salt or quaternary ammonium compound.

As examples of the radicals represented by $T^2$, $T^3$ and $T^4$ there may be mentioned alkyl such as methyl, ethyl, n-propyl, n-butyl and octadecyl, hydroxy lower alkyl such as β-hydroxyethyl and cyclohexyl.

The acids used to form salts with the amino groups or which contain the anion W can be any inorganic acid or an organic acid, such as hydrochloric acid, sulphuric acid, benzene sulphonic acid methane sulphonic acid or benzoic acid. It is especially preferred that the anion W is that arising form the formation of the quaternary ammonium group, for example chloride, bromide or methosulphate.

The preparation of these dispersing agents is described in our earlier granted patent, GB 1373660.

Alternatively, the dispersing agent is the reaction product of a poly(lower alkylene) imine with a polyester having a free carboxylic acid group. The preferred polyester is derived from a hydroxycarboxylic acid of the formula 3

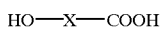

as hereinbefore defined.

The polyester is preferably reacted with the poly (lower alkylene) imine in a weight ratio between 1:1 and 50:1, and more preferably between 2:1 and 20:1.

The term lower alkylene refers to an alkylene group containing from 2 to 4 carbon atoms and the preferred poly(lower alkylene) imine is polyethylene imine which is available either in a substantially linear form or in a branched form. Preferably the polyethylene imine is branched and especially highly branched in which at least 20% of the nitrogen atoms are present as tertiary amino groups. The molecular weight of suitable poly(lower alkylene) imines is generally greater than 500, preferably greater than 5000, and more especially in the range from 10,000 to 100,000.

The reaction product of the hydroxycarboxylic acid and the poly(lower alkylene) imine is a salt or an amide depending on the severity of the reaction conditions employed. The salt and/or amide may be partially neutralised with an acid, especially mineral acid or it may be alkylated, the alkyl group added being optionally substituted, by reaction with an alkyl sulphate such as dimethylsulphate, whereupon a salt is also formed.

The preparation of the reaction product of the hydroxycarboxylic acid and poly(lower alkylene) imine is described in GB 2,001,083.

A particularly useful dispersing agent is the reaction product obtained from approximately 2 moles of poly(12-hydroxystearic acid) with an acid value of 35 mg KOH/gm and 1 mole dimethylaminopropylamine and quaternised with dimethylsulphate as described in Comparative Example C of EP 127,325. This dispersing agent is hereinafter referred to as "Dispersant 1".

A further particularly useful dispersing agent is the reaction product obtained from approximately 3.3 weight equivalents of poly(12-hydroxystearic acid) and 1 weight equivalent of polyethyleneimine with an average molecular weight of about 20,000. This was prepared in a similar manner to Agent A in GB 2,001,083 and is hereinafter referred to as "Dispersant 2".

The amount of dispersant, if present, is preferably from 0.1 to 20%, more preferably from 1 to 10%, especially from 3 to 10% and most especially form 3 to 7% by weight based on the total weight of the composition. The composition also preferably contains a stabiliser to inhibit sedimentation on storage. Examples of stabilisers are naturally occurring clays such as bentonite and particularly organically modified bentonite clay and high MW polymers such as PVC.

As disclosed hereinbefore the ABIT is used as a biocide and especially a fungicide for the protection of plastics materials, especially organic polymeric plastics materials from microbiological degradation. The ABIT is particularly suitable for polyurethane materials and especially organic polymeric materials containing a plasticiser or stabiliser such as those derived from polymerised polyvinylhalides such as polyvinylchloride (PVC). Plasticised PVC is widely used both in the home and industry and is used in clothing, furnishing, shower curtains, flooring, waterproof membranes and the like where the article containing or made from the PVC is exposed to damp or moist conditions.

The amount of plasticiser present in the plastics material varies within wide limits and is determined by the degree of flexibility require in the fabricated material. It is typically between form 1 to 50% by weight of the plastics material.

Thus, as a still further aspect of the invention there is provided a composition comprising an ABIT and a plastics material.

The ABIT's are made by processes already known to the art such as those process disclosed in GB 484,130 wherein a 2-chlorosulphenyl benzoyl chloride is reacted with an alkylamine or an aralkylamine.

Some of the ABIT's are novel. Thus, as a further aspect of the invention there is provided a compound of formula 1 wherein R is —CH(CH$_3$)CH$_2$CH$_2$CH$_3$, —CH(C$_2$H$_5$)CH$_2$CH$_3$, —CH$_2$CH$_2$CH(CH$_3$)CH$_3$, —CH$_2$CH(CH$_3$)CH$_3$, —CH$_2$CH(CH$_3$)C$_2$H$_5$ and cyclopentyl and R$^1$ and n are as defined hereinbefore.

The present invention in all aspects is further illustrated and described in the following examples in which all parts are by weight unless indicated to the contrary.

EXAMPLE 1 AND COMPARATIVE
EXAMPLE A

An agar recipe was prepared from Potato Dextrose Agar (2 parts; ex Oxoid), Tryptone Soya Broth (10 parts; ex Oxoid) and Agar (14 parts; ex Oxoid) made up to 1 litre and having a pH of 6.5. Aliquots of the ABIT under test were added from a 0.1% w/w solution in dioctylphthalate diluted to 3 ml with dioctylphthalate to give a final concentration in the agar recipe of 1.25, 2.5, 5, 20 and 30 ppm. After adding the solution of ABIT to the agar and homogenising, plates were cast and allowed to set. These plates were then inoculated with 10$^5$ spore suspension of the following fungal deteriogens for plastics materials.

| | | |
|---|---|---|
| Aureobasidium pullulans (AP) | CM1 | 145194 |
| Fusarium solanii (FS) | CM1 | 172506 |
| Penicillium funiculosum (PF) | CM1 | 114933 |
| Scopulariopsis brevicaulis (SB) | CM1 | 49528 |
| Streptoverticillium waksmanii (SW) | NCIB | 1091 |

The inoculated plates were incubated for 4 days at 20° C. and the concentration of the ABIT determined at which fungal growth was suppressed. The results are given in Table 1 below which refer to the ABIT of formula 1 wherein n is zero and R is as indicated. These show that the 2-ethyl- and 2-(n-propyl)-BIT exhibit overall slightly superior activity compared with the control and better activity against both AP and SB. 2-ethyl-BIT is more active against FS.

TABLE 1

| Example or Comp Example | R | AP | FS | PF | SB | SW |
|---|---|---|---|---|---|---|
| A | Ethyl | 20 | 5 | 1.25 | 20 | 1.25 |
| 1 | n-propyl | 20 | 20 | 1.25 | 20 | 1.25 |
| Control | — | 30 | 20 | 1.25 | 30 | 1.25 |

Footnote to Table 1
Control is 2-(n-octyl)-isothiazolin-3-one.

EXAMPLE 2 AND COMPARATIVE EXAMPLES B TO D

Example 1 was repeated with the following ABIT's as indicated in Table 2 below and the concentration of chemical determined at which fungal growth was suppressed. The results are given in Table 2 below and show that the 2-(n-butyl)-BIT is more active against the five fungal deteriogens for plastics material than both the 2-(n-hexyl) and 2-(n-octyl)-BIT compounds disclosed in EP 475,123 including higher activity against SB, especially when compared with 2-(n-octyl)-BIT. In general, the 2-(n-butyl)-BIT is similar to control. Taken with the results of Example 1 there is a general trend of decreasing activity against the plastics material deteriogens as the length of the alkyl chain of the ABIT is increased. The 2-benzyl-BIT exhibits an activity which is intermediate between the (n-hexyl)- and 2-(n-octyl)-BIT's. This decrease in activity with increasing number of carbon atoms in the 2-alkyl chain of the ABIT found for these important fungal deteriogens for plastics material is opposite to that disclosed for fungi such as *Aspergillus niger* as disclosed in EP 475,123.

TABLE 2

| Example or Comp Example | R | AP | FS | PF | SB | SW |
|---|---|---|---|---|---|---|
| 2 | n-butyl | 5 | 20 | 1.25 | 1.25 | 5 |
| B | n-hexyl | 5 | >30 | 2.5 | 2.5 | 20 |
| C | n-octyl | >30 | >30 | >30 | 20 | >30 |
| D | benzyl | 30 | >30 | 2.5 | 5 | 30 |
| Control | — | | 1.25 | 20 | 1.25 | 2.5 |

Footnote to Table 2
Control is as stated in Example 1.

EXAMPLES 3 AND 4 AND COMPARATIVE EXAMPLES E AND F

Example 1 was again repeated with the ABIT's listed in Table 3 except that a 50/50 mixture of dioctylphthalate and dioctyladipate was used in place of the dioctylphthalate used in Example 1. The results given in Table 3 below show that n-pentyl-BIT exhibits similar activity to the Control and is superior to n-heptyl-BIT especially against AP and FS. These results are again consistent with decreasing activity as the 2-alkyl chain length of the ABIT is increased. The branched chain compound, 2-ethylbutyl-BIT (Comparative Example E of Table 3) exhibits similar activity to the straight chain analogue (Comparative Example B of Table 2) with some loss of activity against PF. The 2-phenylethyl compound exhibits very high activity against all five deteriogens and is superior in this aspect to the 2-(n-alkyl)-BlT's and also the 2-benzyl-BIT (Comparative Example D of Table 2).

TABLE 3

| Example as Comp Example | R | AP | FS | PF | SB | SW |
|---|---|---|---|---|---|---|
| 3 | n-pentyl | 5 | 20 | 1.25 | 1.25 | 1.25 |
| E | 2-ethylbutyl | 5 | 30 | 20 | 1.25 | 20 |
| F | n-heptyl | 20 | >30 | 2.5 | 1.25 | 1.25 |
| 4 | 2-phenylethyl | 1.25 | 1.25 | 1.25 | 1.25 | 1.25 |
| Control | — | 2.5 | 20 | 2.5 | 1.25 | 1.25 |

Footnote to Table 3
Control is as indicated in Table 1.

EXAMPLES 5 TO 7 AND COMPARATIVE EXAMPLE A

The ABIT's listed in Table 4 below were heated in air on a Differential Scanning Calorimeter (DSC) from 25–300° C. at a 10° C./minute heating rate and the temperature stability determined together with the temperature above which evaporation occurred and also the weight loss by 160° C. which represents the temperature at which PVC is fabricated. These results indicate that at least 3 carbon atoms in the alkyl chain of the ABIT is required for adequate thermal stability to withstand the fabrication temperatures for PVC plastics materials. When these results are combined with the antifungal data of Examples 1 to 4 the ABIT wherein R represents $C_{3-5}$-alkyl is the optimal compromise for a fungicide to protect against fungal deteriogens in plasticised PVC plastics materials. The activity of 2-phenylethyl-BIT combined with its physical properties such as thermal stability show this compound to be superior as an antifungal agent for PVC plastics materials compared with 2-alkyl-BIT's especially when compared with the activity of 2-benzyl-BIT as recorded in Example 2.

TABLE 4

| Example No. | R | Stability temp (° C.) | Start of evaporation (° C.) | Weight loss (%) by 160° C. |
|---|---|---|---|---|
| 5 | n-propyl | 240 | 130 | 5.5 |
| 6 | n-butyl | 260 | 96 * | 5.1 |
| 7 | 2-phenylethyl | >250 | >200 | 0 |
| A | ethyl | 235 | 107 | 10.6 |

Footnote to Table 4
* low figure is thought due to a trace of solvent

EXAMPLES 8 TO 15 AND COMPARATIVE EXAMPLES A, G AND H

The fungal esterase activity in PVC was determined by the following fluorescein diacetate protocol.

PVC coupons were prepared by adding the ABIT from the requisite aliquot of a 1% (w/w) solution of the compound dissolved in 50/50 dioctylphthalate and dioctyladipate to give 100, 250, 750, 2250 and 6750 ppm chemical in the final PVC coupon.

The PVC coupon had the following composition:
100 parts, PVC resin (Corvic S 67/100)
2 parts, Zn/Ca stabiliser (Lankromark LN 138)
3 parts, Co plasticiser (Lankroflex ED6)
25 parts, plasticiser (di-iso-octylphthalate) (DOP)
25 parts, plasticiser (di-octyladipate) (DOA)
0.5 parts, calcium stearate dispersant
0.2 parts, stearic acid mould-release agent
ppm ABIT A PVC sheet was prepared by mixing the above ingredients until homogeneous and then rolling and mixing on a two-roll mill for 90 seconds at 160° C.

The sheet was then cut into pieces and coupons (2 cm×5 cm) were prepared by pressing between steel sheets at 160° C. and 8 tons pressure for 5 minutes.

Duplicate PVC coupons were placed on the surface of moistened vermiculate beds and sprayed with a 105 fungal spore suspension of the five fungal deteriogens listed in Example 1 which had been prepared in a minimum salts solution comprising 2.0 parts sodium nitrate, 0.7 part potassium dihydrogen phosphate, 0.3 part dipotassium hydrogen phosphate, 0.5 part potassium chloride, 0.5 part, magnesium sulphate heptahydrate and 0.01 part ferrous sulphate heptahydrate all in 1 litre giving a pH value of 6 to 6.5.

The inoculated coupons were then incubated for 7 days at 21° C. The coupons were then removed and placed in individual bottles containing 6 ml buffer solution at pH 7.6 prepared form 0.06M disodium hydrogen phosphate (862.5 ml) and 0.06M sodium dihydrogen orthophosphate (137.5 ml) and also 1 ml fluorescein diacetate (FDA) in dry acetone. The samples were then incubated for 30 minutes at 37° C. in order to develop the colour reaction. The absorbance of each solution was measured at 490 nm using a spectrophotometer. This colour reaction is a measure of esterase expressed by the fungi and indicates fungal deterioration of the plasticiser.

Prior to evaluation by FDA analysis, the coupons were also assessed visually for fungal growth using a stereomicroscope after 1 months incubation at 25° C. and 95% relative humidity.

Parallel experiments were also carried out on coupons which had been weathered for 100 hours in an Atlas ES25 Weatherometer at cam setting 7 with a 2 minute water cycle every 10 minutes and continuous UV radiation.

The results are given in Tables 5 and 6 below.

The FDA analysis of Table 5 for the unweathered samples at the 100 and 250 ppm level confirms the reduction in activity against the five fungal deteriogens for plastics materials with increasing number of carbon atoms in the 2-alkyl chain. This is manifest even though some loss of ABIT must have occurred in the case of the lower alkyl chain analogues during fabrication of the coupons. After weathering, however, the trend is reversed and protection against the fungi increased with the increasing number of carbon atoms in the 2-alkyl group. This is most clearly seen at the 750 ppm level of ABIT.

The trend in the fungal growth data of Table 6 is less clear although there is again a trend to reduced activity with increasing number of carbon atoms in the 2-alkyl group. This is most clearly shown by the unweathered data at 250 and 750 ppm applied ABIT. The trends after weathering are less clear. However, when the data of Tables 1 to 6 are combined, ABIT's suitable for plastics materials are a compromise between high temperature stability, volatility and activity against fungal deteriogens. In the case of ABIT's containing a 2-alkyl chain, this compromise is centred on the 2-($C_{3-5}$-alkyl)-BIT's.

TABLE 5

FDA ANALYSIS

| Example and Comp example | R | weathering | Test chemical concentration (ppm) | | | | |
|---|---|---|---|---|---|---|---|
| | | | 100 | 250 | 750 | 2250 | 6750 |
| 8 | n-propyl | u | sl | tr | — | — | ND |
| | | w | ++ | ++ | sl | — | ND |
| 9 | n-butyl | u | sl | sl | — | — | ND |
| | | w | + | ++ | tr | — | ND |
| 10 | n-pentyl- | u | tr | — | — | — | ND |
| | | w | tr | sl | — | — | ND |
| 11 | 2-phenyl-ethyl | u | — | — | — | — | ND |
| | | w | tr | — | — | — | |
| A | ethyl | u | tr | — | — | — | ND |
| | | w | ++ | sl | ++ | — | ND |
| G | | u | ND | sl | sl | — | — |
| | | w | ND | + | sl | — | — |
| H | | u | + | | | | |
| | | w | ++ | | | | |
| Control | | u | ++ | | | | |
| | | w | ++ | | | | |

Footnote to Table 5
u is unweathered
w is weathered
ND is not determined
G is trichloromethylmercaptophthalimide
H is oxy-bis-10,10-phenoxarsine
- is no absorbance at 490 nm
tr is less than 0.1 absorbance at 490 nm
sl is 0.1–0.25 absorbance at 490 nm
+ is 0.25–0.5 absorbance at 490 nm
++ is greated than 0.5 absorbance at 490 nm

TABLE 6

| Example and Comp Example | R | weathering | Test chemical concentration (ppm) | | | | | |
|---|---|---|---|---|---|---|---|---|
| | | | 100 | 250 | 300 | 750 | 2250 | 6750 |
| 12 | n-propyl | u | 3,3 | 0,0 | ND | 0,0 | 0,0 | ND |
| | | w | 5,5 | 5,5 | ND | 3,3 | 0,0 | ND |
| 13 | n-butyl | u | 1,1 | 1,1 | ND | 0,0 | 0,0 | ND |
| | | w | 5,5 | 4,5 | ND | 4,5 | 0,0 | ND |
| 14 | n-pentyl | u | 4,4 | 3,2 | ND | 2,3 | 2,1 | ND |
| | | w | 4,3 | 4,4 | ND | 3,2 | 3,3 | ND |
| 15 | 2-phenyl-ethyl | u | 4,2 | 0,0 | ND | 0,0 | 0,0 | ND |
| | | w | 5,5 | 5,5 | ND | 3,3 | 0,0 | ND |
| A | ethyl | u | 1,1 | 0,0 | ND | 0,0 | 0,0 | ND |

TABLE 6-continued

| Example and Comp Example | R | weathering | Test chemical concentration (ppm) | | | | | |
|---|---|---|---|---|---|---|---|---|
| | | | 100 | 250 | 300 | 750 | 2250 | 6750 |
| | | w | 5,5 | 3,2 | ND | 4,2 | 0,0 | ND |
| G | | u | ND | 2,2 | ND | 1,1 | 1,1 | 0,0 |
| | | w | ND | 4,3 | ND | 2,2 | 1,1 | 0,0 |
| H | | u | 4,4 | ND | 0,0 | ND | ND | ND |
| | | w | 5,5 | ND | 5,5 | ND | ND | ND |
| Control | | u | 5,5 | ND | | | | |
| | | w | 5,5 | ND | | | | |

Footnote to Table 6
The legends n,w, and ND have the same meaning as in Table 5
G is trichloromethylcercaptophthalimide
H is oxy-bis-10,10-phenoxarsine
0 is no growth on test pieces
1 is less than 1% surface growth
2 is 1–10% surface growth
3 is 10–30% surface growth
4 is 30–70% surface growth
5 is greater than 70% surface growth

EXAMPLE 16 a) Preparation of 2,2'-dithiodi-N-(3-methylbutyl)-dibenzamide

Dithiodibenzoyl chloride (6.86 parts, 0.02M) was added in portions with stirring at 0 to 5° C. to a solution of isoamylamine (3.47 parts, 0.04M ex Aldrich) and triethylamine (4.04 parts, 0.04M ex Aldrich) in diethylether. An immediate precipitate formed. The reaction mix was stirred for 16 hours whilst allowing the temperature to rise to about 20° C. The ether was then evaporated and the product washed with methanol (50 ml) and water (50 ml). The product was finally recrystallised from methanol as a white solid (6 parts, 69% theory, mp=181–183° C.

Elemental analysis: Theory: 64.8%C, 7.3%H, 6.3%N, 14.4%S. Found: 64.1%C, 6.9%H, 6.3%N, 14.4%S.

b) Preparation of 2-(3-methylbutyl)-benzisothiazolin-3-one

The bisamide (5.7 part, 0.0128M) prepared as described above was dissolved in pyridine (75 ml) and iodine (3.26 parts, 0.0128M) was added portionwise with stirring at 20 to 25° C. Initially, the iodine was rapidly decolourised but towards the end of the addition of iodine the reaction mix became yellow-brown. After stirring for a further 2 hours at 20 to 25° C. the reaction mix became almost colourless. The pyridine was then evaporated and the product dissolved in toluene which was washed with aqueous sodium thiosulphate followed with water to remove traces of iodine. The toluene was then evaporated giving a pale yellow oil (5.3 parts, 94% theory) which solidified on standing. The product was recrystallised from hexane mp=55–56° C.

Elemental analysis Theory: 65.1%C, 6.6%H, 6.4%N, 14.6%S. Found: 65.1%C, 6.8%H, 6.3%N, 14.5%S.

EXAMPLE 17

Preparation of 2-(1-methylbutyl)benzisothiazolin-3-one

2-Chlorosulphenylbenzoyl chloride (6 parts, 0.029M) dissolved in diethylether (30 ml) was added dropwise at 0 to 3° C. to a stirred solution of 1-methylbutylamine (7.36 parts, 0.84M ex Aldrich) in diethylether (30 ml). The reactants were stirred for 16 hours whilst allowing the temperature to rise to about 20° C. The ether solution was then screened, washed with water and dried over magnesium sulphate. After evaporation of the ether, the product was obtained as a pale yellow gum (5.5 parts, 86% theory) which gradually solidified on standing. This was recrystallised from hexane. mp=52–54° C.

Elemental analysis Theory 65.3%C, 7.2%H, 6.5%N, 14.4%S. Found 65.1%C, 6.8%H, 6.3%N, 14.5%S.

EXAMPLE 18

Preparation of 2-(1-ethylpropyl)benzisothiazolin-3-one

This was prepared in analogous manner to that described in Example 17 except using 2-chlorosulphonyl chloride (6.21 parts, 0.03M) and 1-ethylbutylamine (8.7 parts, 0.2M ex Aldrich). The product was obtained as a pale yellow gum (6.4 parts, 96% theory) which solidified on standing. It was recrystallised from hexane mp=80–82° C.

Elemental analysis Theory: 64.8%C, 5.7%H, 6.3%N, 14.50%S. Found: 65.1%C, 6.8%H, 6.3%N, 14.5%S.

EXAMPLE 19

Preparation of 2-cyclopentylisothiazolin-3-one

This was prepared in analogous manner to that described in Example 17 except using 2-chlorosulphenylbenzoyl chloride (5.175 parts, 0.025M) and cyclopentylamine (8.52 parts, 0.1M ex Aldrich). The product was obtained as a yellow oil (5.9 parts) which was recrystallised form hexane mp 87–88° C.

EXAMPLE 20

Preparation of 2-(2-methylpropyl) benzisothiazolin-3-one

This was prepared by the process described in Example 17 except using 2-chlorosulphenylbenzoyl chloride (4.14 parts, 0.02M) and isobutylamine (7.95 parts, 0.08M). The product (4 parts, 97% theory) was obtained as a pale yellow oil.

EXAMPLES 21 TO 25

The following bisamides of formula A were prepare by the process described in Example 19(a) and converted to the substituted benzoisothiazolin-3-one (BIT) of formula B by the process described in Example 19(b).

A

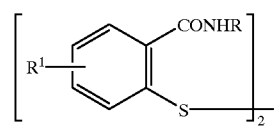

-continued

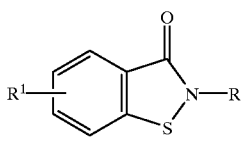

The analytic data and melting points are given in Tables 7a and 7b below wherein the position of substituent R¹ is given for the BIT.

The 2-alkyl BIT's and 2-aralkyl-BIT's, the preparation of which is described in Examples 21 to 25, exhibit similar protection to 2-n-butyl-BIT against deteriogens for plastics materials.

TABLE 7a

| | | | BISAMIDE ELEMENTAL ANALYSIS (%) | | | | | | | |
|---|---|---|---|---|---|---|---|---|---|---|
| | | | THEORY | | | | FOUND | | | mp |
| Example | R | R¹ | C | H | N | S | C | H | N | S | (° C.) |
| 21 | —CH₂CH(CH₃)C₂H₅ | H | 64.9 | 7.2 | 6.3 | 14.4 | 65.1 | 7.3 | 6.3 | 12.8 | 174–5 |
| 22 | —(CH₂)₂CH₃ | 6Cl— | | | | | | | | | |
| 23 | —(CH₂)₂Ph | 6Cl— | 62.0 | 4.5 | 4.8 | 11.0 | 62.0 | 4.5 | 4.9 | 11.0 | 240–2 |
| 24 | —(CH₂)₃CH₃ | 6Cl— | | | | | | | | | |
| 25 | —(CH₂)₃CH₃ | 5Cl— | 55.2 | 5.4 | 5.8 | 13.2 | 55.1 | 5.4 | 5.8 | 13.9 | 230–2 |

TABLE 7b

| | | | BIT ELEMENTAL ANALYSIS (%) | | | | | | | |
|---|---|---|---|---|---|---|---|---|---|---|
| | | | THEORY | | | | FOUND | | | mp |
| Example | R | R¹ | C | H | N | S | C | H | N | S | (° C.) |
| 21 | —CH₂CH(CH₃)C₂H₅ | H | 65.2 | 6.8 | 6.3 | 14.5 | 64.6 | 6.8 | 6.0 | 14.1 | OIL |
| 22 | —(CH₂)₂CH₃ | 6Cl— | 52.8 | 4.4 | 6.2 | 14.1 | 53.2 | 4.5 | 6.6 | 13.6 | |
| 23 | —(CH₂)₂Ph | 6Cl— | 62.2 | 4.1 | 4.8 | 11.0 | 62.7 | 4.1 | 5.0 | 11.3 | 143–5 |
| 24 | —(CH₂)₃CH₃ | 6Cl— | 54.7 | 5.0 | 5.8 | 13.3 | 55.5 | 5.1 | 6.0 | 13.5 | 105–6 |
| 25 | —(CH₂)₃CH₃ | 5Cl— | 54.7 | 5.0 | 5.8 | 13.3 | 56.1 | 5.1 | 6.0 | 14.2 | 75–6 |

I claim:

1. A method for the protection of a thermoplastic material against fungi which comprises adding to the thermoplastic material a fungicidally effective amount of a 2-alkyl- or 2-aralkyl-BIT of formula

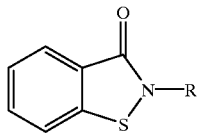

wherein
R is $C_{3-5}$-alkyl or aralkyl which contains at least two carbon atoms linking the aryl group to the nitrogen atom.

2. A method as claimed in claim 1 wherein R contains 4 carbon atoms.

3. A method as claimed in claim 1 wherein the BIT derivative is 2-(n-butyl)-BIT or 2-phenylethyl-BIT.

4. A method as claimed in claim 1 wherein the amount of the BIT is less than 0.5% w/w of the thermoplastic material.

5. A composition comprising a plasticiser or stabiliser and a 2-alkyl or 2-aralkyl-BIT derivative of formula 1.

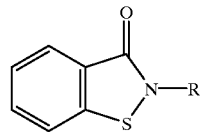

wherein
R is $C_{3-5}$-alkyl or aralkyl which contains at least 2 carbon atoms linking the aryl group to the nitrogen atom.

6. A composition as claimed in claim 5 wherein the plasticiser or stabiliser is in an ester or epoxidised vegetable oil.

7. A composition as claimed in claim 6 wherein the ester is dioctylphthalate, dioctyladipate or mixture thereof.

8. A composition as claimed in claim 6 wherein the vegetable oil is soya bean oil.

9. A composition as claimed in any one of claims 5 to 8 which further comprises a dispersant.

10. A composition which comprises a thermoplastic material and a 2-alkyl or 2-aralkyl-BIT derivative of Formula 1

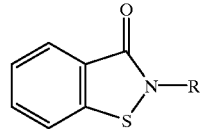

wherein

R is C$_{3-5}$-alkyl or aralkyl which contains at least 2 carbon atoms linking the aryl group to the nitrogen atom.

11. A composition as claimed in claim 10 wherein the thermoplastic material is polyurethane or plasticiser PVC.

12. A composition which comprises a thermoplastic material and a 2-alkyl or 2-aralkyl-BIT derivative of Formula I

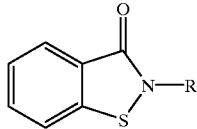

wherein
R is C$_{3-5}$-alkyl or aralkyl which contains at least 2 carbon atoms linking the aryl group to the nitrogen atom, said thermoplastic material being one which is fabricatable at temperatures in excess of 140° C. and said BIT derivative being characterized by its stability and low volatility under such conditions.

13. A method for the protection of a thermoplastic material against fungi which comprises adding to the thermoplastic material a fungicidally effective amount of a 2-alkyl- or 2-aralkyl-BIT of formula

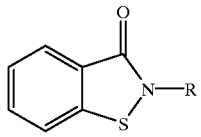

wherein
R is C$_{3-5}$-alkyl or aralkyl which contains at least two carbon atoms linking the aryl group to the nitrogen atom, said thermoplastic material being one which is fabricatable at temperatures in excess of 140° C. and said BIT derivative being characterized by its stability and low volatility under such conditions.

14. The method of claim 1 wherein the weight loss of the 2-alkyl- or 2-aralkyl-BIT is less than 10% when heating the thermoplastic material containing the 2-alkyl- or 2-aralkyl-BIT from 25 to 160° C.

15. A composition comprising a plasticizer or stabilizer and a 2-alkyl or 2-aralkyl-BIT derivative of Formula 1:

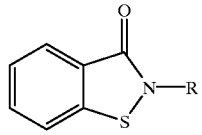

wherein
R is C$_{3-5}$-alkyl or aralkyl which contains at least 2 carbon atoms linking the aryl group to the nitrogen atom wherein the weight loss of the 2-alkyl- or 2-aralkyl-BIT is less than 10% when heating the composition containing the 2-alkyl- or 2-aralkyl-BIT from 25 to 160° C.

16. In a method of fabricating a plastics material at elevated temperature, the improvement wherein the plastics material is protected against fungi by adding to the plastics material, before its fabrication, a fungicidally effective amount of a 2-alkyl- or 2-aralkyl-BIT of formula

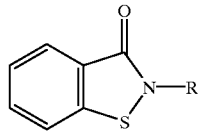

wherein
R is a C$_{3-5}$-alkyl or aralkyl which contains at least two carbons atoms linking the aryl group to the nitrogen atom.

* * * * *

UNITED STATES PATENT AND TRADEMARK OFFICE
CERTIFICATE OF CORRECTION

PATENT NO.     : 6,005,032
DATED          : December 21, 1999
INVENTOR(S)    : Austin It is certified that error appears in the above-identified patent and that said Letters Patent is hereby corrected as shown below:

<u>Column 14,</u>
Line 49, delete "in".

Signed and Sealed this

Nineteenth Day of August, 2003

JAMES E. ROGAN
*Director of the United States Patent and Trademark Office*